United States Patent [19]

Kohda et al.

[11] Patent Number: 4,727,420

[45] Date of Patent: Feb. 23, 1988

[54] ACOUSTOOPTIC IMAGE FORMATION

[75] Inventors: Katsuhiro Kohda; Junji Miyahara, both of Kanagawa, Japan

[73] Assignee: Fuji Photo Film Co., Ltd., Kanagawa, Japan

[21] Appl. No.: 787,850

[22] Filed: Oct. 16, 1985

[30] Foreign Application Priority Data

Oct. 16, 1984 [JP] Japan ............................... 59-216903
Apr. 11, 1985 [JP] Japan ................................ 60-77206
May 17, 1985 [JP] Japan ............................... 60-105579

[51] Int. Cl.$^4$ ............................................ H04N 5/32
[52] U.S. Cl. .................................... 358/112; 358/294
[58] Field of Search ............... 358/209, 112, 294, 293, 358/111; 250/311, 327.2

[56] References Cited

U.S. PATENT DOCUMENTS 4,092,174 5/1978 Ellis et al. ............................ 106/53
4,258,264 3/1981 Kotera et al. ..................... 250/327.2

FOREIGN PATENT DOCUMENTS 56-9465 3/1981 Japan .

OTHER PUBLICATIONS

"Photoacoustic Spectroscopy and It's Application-PAS," Japan Spectral Society Measurement Series Edited by Shiroh Sawada published by Scientific Society Publishing Center.
"Photochromic Glass" by Takeo Ichimura, Ceramic Technology Collection, pp. 423-429 (1979) Industrial Technology Center.
"Inorganic Photochromic Materials-Compound and Glass" by Sumio Sakuhana, Material Chemistry 8, pp. 191-202 (1971).
"Photochromic Glasses and Inorganic Compounds" by Sumio Sakuhana, Chemical Industry 62, pp. 189-194 (1978).

Primary Examiner—L. T. Hix
Assistant Examiner—D. Rutledge
Attorney, Agent, or Firm—Sughrue, Mion, Zinn, Macpeak, and Seas

[57] ABSTRACT

An acoustooptic image can be formed by using a plate-like image sensor capable of increasing its optical density upon exposure to a radiation. The image sensor is exposed to a radiation bearing image information to record the image information on the image sensor. Then, pulsed light is applied to the image sensor to enable the same to generate a pressure wave commensurate with the recorded image information. The pressure wave is detected in synchronism with the pulsed light and converted into an electric signal, from which an image signal is reproduced. The image signal may be displayed on a CRT, or recorded on a magnetic recording medium, or reproduced on a photographic material.

38 Claims, 12 Drawing Figures

ACOUSTOOPTIC IMAGE FORMATION

BACKGROUND OF THE INVENTION

1. Field of the Invention

The present invention relates to a method of and a device for acoustooptically forming images by applying light to a recording medium having different optical densities representative of an image to generate an image-dependent pressure wave.

2. Description of the Prior Art

Various processes are used in the art of forming or reproducing images recorded on recording mediums. Cameras for photographing radiation images are also known. One conventional radiographic camera is an X-ray camera using an X-ray photographic film as the recording medium. However, the formation of an image based on the optoacoustic effect is not known in the art.

Summary of the Invention

Images recorded as optical density differences on a recording medium can be acoustooptically reproduced by irradiating the recording medium with pulses of light, detecting pressure fluctuations or a pressure wave generated from the recording medium in synchronism with the light pulses applied to the recording medium, and utilizing a detected electric signal indicative of the pressure wave as an image signal.

Methods and devices for such acoustooptic image formation are totally novel and no prior art relevant thereto is known. The principles of the acoustooptic effect are disclosed in Japan Spectral Society Measurement Series 1 "Photoacoustic spectroscopy and its applications-PAS" edited by Shiroh Sawada and published by Scientific Society Publishing Center.

It is an object of the present invention to provide a novel method of acoustooptically forming images.

Another object of the present invention to provide a novel device for acoustooptically forming images.

Still another object of the present invention is to provide a novel camera utilizing the acoustooptic effect in forming images.

According to the present invention, there is provided a method of forming an acoustooptic image by using a plate-like image sensor capable of increasing its optical density upon exposure to a radiation, the method comprising the steps of exposing the image sensor to a radiation bearing image information to record the image information on the image sensor, applying pulsed light to the image sensor to enable the same to generate a pressure wave commensurate with the recorded image information, detecting the pressure wave in synchronism with the pulsed light to convert the pressure wave into an electric signal, and reproducing an image from the electric signal.

According to the present invention, there is also provided a device for forming an acoustooptic image, comprising a plate-like image sensor capable of increasing its optical density upon exposure to a radiation, first exposing means for exposing the image sensor to a radiation bearing image information to record the image information on the image sensor, second exposing means for applying pulsed light to the image sensor to enable the same to generate a pressure wave commensurate with the recorded image information, detecting means for detecting the pressure wave in synchronism with the pulsed light to convert the pressure wave into an electric signal, and image reproducing means for reproducing an image from the electric signal.

According to the present invention, there is further provided an acoustooptic camera comprising a light-shielding housing for accommodating a plate-like image sensor capable of increasing its optical density upon exposure to a radiation, the light-shielding housing having means for exposing the image sensor to a radiation bearing image information to record the image information on the image sensor, second exposing means in the light-shielding housing for applying pulsed light to the image sensor to enable the same to generate a pressure wave commensurate with the recorded image information, and detecting means in the light-shielding housing for detecting the pressure wave in synchronism with the pulsed light to convert the pressure wave into an electric signal.

The image derived from the electric signal may be displayed on a CRT, or recorded on a magnetic tape or a magnetic disc, or reproduced on a photographic material.

The pressure wave may be detected by a microphone, a bolometer, a piezoelectric device, or an electrostrictive device.

Exposure of the image sensor to the pulsed light may be effected by scanning the image sensor with a light beam spot through two-dimensional scanning process, or with a one-dimensional fan beam, or by applying the pulsed light to the image sensor over its entire surface.

The image sensor may be in the form of a stimulable phosphor sheet, a diazo film, a silver-salt film, or a photochromic material.

The above and other objects, features and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
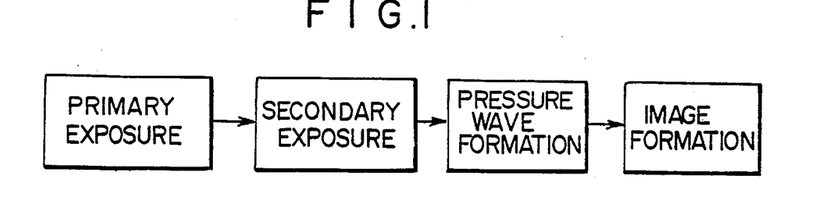
FIG. 1 is a block diagram showing progressive steps of a method of acoustooptically forming an image according to the present invention.

FIG. 1 shows the essential steps of a method of acoustooptically forming an image according to the present invention. The method of the invention is basically composed of four steps: primary exposure, secondary exposure, pressure wave detection, and image formation.

In the first step of primary exposure, a plate-like image sensor is used which will exhibit an increase in optical density upon exposure to a radiation such as visible light, an X-ray, an electron beam, an ultraviolet ray, an α-ray, a β-ray, or a γ-ray, and the plate-like image sensor is exposed to the radiation carrying image information so as to record the image information as optical density differences on the image sensor. In the second step of secondary exposure, the image sensor is exposed to pulses of light to enable the image sensor to generate pressure fluctuations or a pressure wave dependent on the recorded image information in synchronism with the applied pulses of light. The third step detects the pressure wave with a sound detector such as a microphone. In the fourth step, an electric signal generated by the microphone in proportion to the detected pressure wave is utilized to reproduce the image information on an image reproducing device or material.

The method of the invention will be described in greater detail with reference to FIGS. 2A, 2B, and 3.

Figures 2A, 2B, 3:
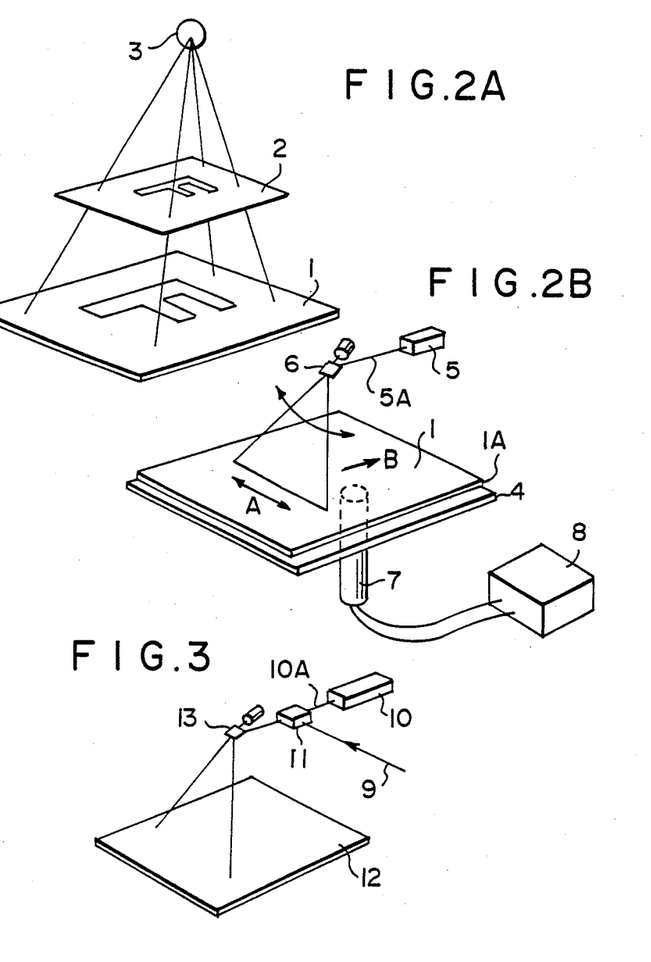
FIG. 2A is a perspective view showing the first step of the method of the invention.
FIG. 2B is a perspective view illustrative of the second and third steps of the method of the invention.
FIG. 3 is a perspective view showing the fourth step of the method of the invention.

In FIG. 2A, a plate-like image sensor 1 employed as an image carrier capable of recording or storing radiation image information may comprise a stimulable phosphor (as disclosed in Japanese Unexamined Patent Publication No. 55(1980)-12429), a diazo film, a silversalt film, or a sheet of photochromic glass. An object 2 such as a film carrying an original image to be recorded is placed over the image sensor 1. The image sensor 1 is then exposed to a radiation such as an X-ray or visible light emitted from a radiation source 3 and transmitted through the object 2. The radiation image of the object 2 is now stored or recorded on the image sensor 1.

Then, as shown in FIG. 2B, the image sensor 1 is placed on a pressure wave guide 4 in intimate contact therewith through the intermediary of an adherent layer 1A. The image sensor 1 is scanned in the directions of the arrow A by a laser beam 5A emitted from a laser beam source 5 above the image sensor 1 and deflected by a galvanometer mirror 6 (main scanning). At the same time, the image sensor 1 is moved in the direction of the arrow B (sub-scanning). Therefore, the image sensor 1 is two-dimensionally scanned by the laser beam 5A. A pressure wave or pressure fluctuations generated by the image sensor 1 and transmitted through the pressure wave guide 4 are collected by a microphone 7 positioned below the pressure wave guide 4. The microphone 7 produces an output electric signal which is applied to an output signal storage circuit 8.

The output signal storage circuit 8 may be replaced with an image reproducing device capable of reproducing the image from the image signal, or with a recording device employing a magnetic tape, a magnetic disk, or other magnetic recording mediums.

In FIG. 3, a laser beam 10A emitted from a laser beam source 10 is modulated by the image signal 9 from the output signal storage circuit 8. The modulated laser beam 10A is then deflected by a galvanometer mirror 13 to scan a recording medium 12 to reproduce the image information thereon.

The photochromic glass, which the image sensor may be made of, is widely used as a material of spectacle lenses. The photochromic glass is described in detail in Japanese Patent Publication No. 56(1981)-9465; and various other publications such as "Photochromic glass and inorganic compound" by Sumio Sakuhana, Chemical Industry 62, p. 189–194 (1978); "Photochromic glass" by Takeo Ichimura, Ceramic Technology Collection p. 423–429 (1979), Industrial Technology Center; "Inorganic photochromic materials—compound and glass—" by Sumio Sakuhana, Material Chemistry 8, p. 191–202 (1971), for example.

The microphone 7 may be replaced with a bolometer for detecting thermal energy produced in proportion to the pressure wave, or an electrostrictive device, or a piezoelectric device capable of electrically detecting a pressure. The piezoelectric device is composed of a piezoelectric material such as crystal, Rochelle salt, potassium tartrate (DKT), potassium primary phosphate (KDT), PZT, polyvinylidene fluoride (PVDF), or polyvinylidene cyanide copolymer [P(VDCN VAc)].

Figure 4A:
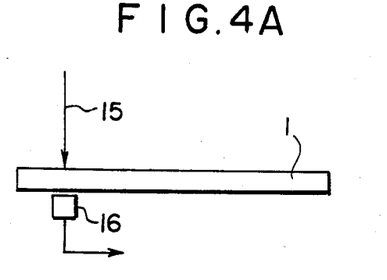
FIG. 4A is a side elevational view illustrating the second and third steps of a method according to another embodiment of the present invention.
Figure 4B:
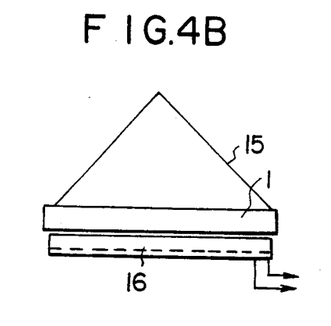
FIG. 4B is a front elevational view explanatory of the second and third steps of FIG. 4A.

FIGS. 4A and 4B show the manner in which pulses of light are applied in the form of a fan beam 15 to the image sensor 1, and a pressure wave generated by the image sensor 1 in response to the applied light pulses is detected by a one-dimensional array detector 16 disposed beneath the image sensor 1. When applying the light pulses to the image sensor 1 for secondary exposure, the fan beam 15 together with the array detector 16, and the image sensor 1 are moved with respect to each other for two-dimensional scanning of the image sensor 1. To this end, the fan beam 15 and the array detector 16 may be moved and the image sensor 1 may be fixed, or vice versa.

Figure 5:
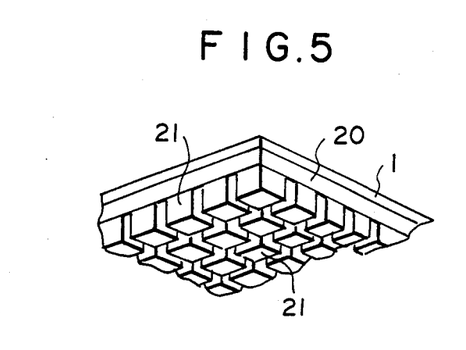
FIG. 5 is a perspective view of a pressure detector according to still another embodiment of the present invention.

FIG. 5 illustrates another arrangement in which a pressure-wave detector 20 is placed coextensively below the image sensor 1 in intimate contact therewith, and a matrix of electrodes 21 is disposed on the entire lower surface of the detector 20. The electrodes 21 can therefore detect a pressure wave generated by the image sensor 1 when the entire surface of the image sensor 1 is exposed to pulses of light. However, the image sensor 1 may be scanned by a beam spot or a fan beam for secondary exposure.

Various acoustooptic cameras according to the present invention will be described with reference to FIGS. 6 through 10. Like or corresponding parts are denoted by like or corresponding reference characters throughout several views.

Figure 6:
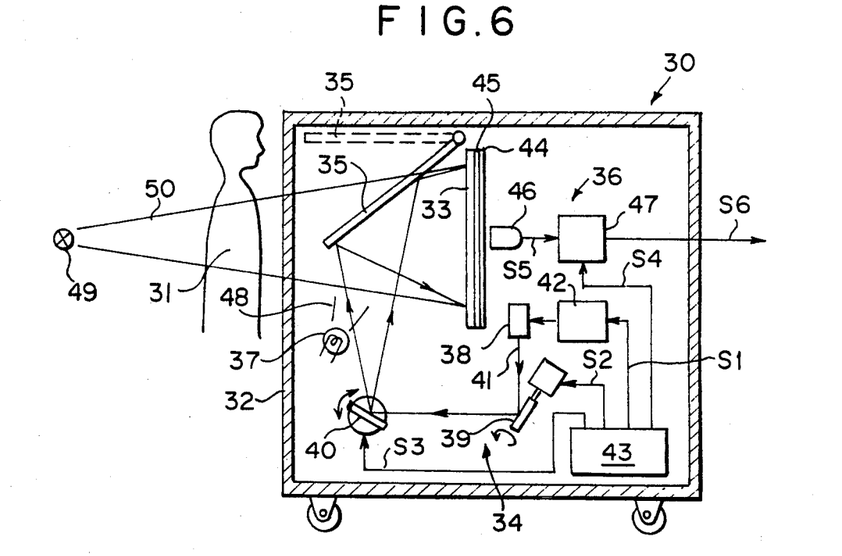
FIG. 6 is a schematic side elevational view of a camera according to an embodiment of the present invention.

FIG. 6 shows an acoustooptic camera according to an embodiment of the present invention. The acoustooptic camera, generally denoted at 30, is designed primarily for photographing the radiation image of an object 31 such as a human body. The acoustooptic camera 30 includes a light-shielding housing 32 accommodating therein a plate-shaped image sensor 33, an exposure assembly 34 for two-dimensionally scanning the image sensor 33 with light transmitted via a movable mirror 35, a pressure-wave detector 36, and an erase light source 37.

The plate-like image sensor 33 may comprise a stimulable phosphor sheet as disclosed in Japanese Unexamined Patent Publication No. 55(1980)-12429. The stimulable phosphor sheet may be in the form of a layer of stimulable phosphor deposited on a sheet-like support, or a sheet of self-supporting stimulable phosphor.

The exposure assembly 34 comprises a laser 38 such as an He-Ne laser or a semiconductor laser, and two light deflectors 39, 40 for deflecting a laser beam 41 emitted as light from the laser 38 into mutually perpendicular directions. The laser beam 41 deflected by the light deflectors 39, 40 is reflected by the movable mirror 35 to impinge on the image sensor 33 for dimensionally scanning the same. Each of the light deflectors 39, 40 may comprise a known light deflector such as a galvanometer mirror, a polygonal mirror, an acousto-optic deflector. The laser 38 is driven by a driver circuit 42 which is controlled by a control signal S1 from a control circuit 43 for energizing the laser 38 to emit laser pulses. The driver circuit 42 may comprise an acousto-optic modulator or a modulator for directly modulating the laser 41 emitted by the laser 38. The light deflectors 39, 40 are controlled by respective control signals S2, S3 generated by the control circuit 43.

The pressure-wave detector 36 has a wave guide 44 against which the image sensor 33 is held through an adherent member 45, a microphone 46 disposed closely to the wave guide 44, and a signal processor 47 for processing an electric pressure-wave (sound) signal issued from the microphone 46.

The erase light source 37 emits light 48 in the stimulation wavelength region as that of the light to be applied to the stimulable phosphor. The light emitted from the erase light source 37 is reflected by the movable mirror 35 to fall on the image sensor 33. Specifically, the erase light source 37 may comprise a xenon flash lamp, a tungsten lamp, an infrared lamp, a fluorescent lamp, or a laser source.

The movable mirror 35 is moved angularly by a driver means (not shown) between the solid-line position and the dotted-line position. The light-shielding housing 32 is made of a material capable of shielding ambient light in the stimulation wavelength region of the stimulable phosphor and also of transmitting a radiation for recording the image of the object 31 on the image sensor 33.

The acousto-optic camera 30 operates to record the image of the object 31 on the image sensor 33 as follows: The acousto-optic camera 30 is disposed to face the image sensor 33 toward a radiation source 49 such as an X-ray tube. The object 31 is positioned between the camera 30 and the radiation source 49, and the movable mirror 35 is retracted from the solid-line position in front of the image sensor 33 toward the dotted-line position. When the radiation source 49 is energized, it emits a radiation 50 which passes through the object 31. The radiation 50 which bears the image of the object 31 them falls on the image sensor 33 to record the radiation image thereon.

The radiation image recorded on the image sensor 33 will then be converted into an electric image signal in the following manner: First, the movable mirror 35 is angularly moved to the solid-line position, and then the pulsed laser beam 41 emitted from the laser 38 is deflected by the light deflectors 39, 40 for two-dimensionally scanning the image sensor 33. When the image sensor 33 is scanned by the pulsed laser beam 41, it generates a pressure wave or pressure pulsations commensurate with the image information stored therein. The generated pressure wave is detected by the microphone 46 which produces an electric pressure-wave signal S5 applied to the signal processor 47. The signal processor 47 is supplied with a synchronizing signal S4 generated by the control circuit 43 in synchronism with the pulsed laser beam 41 for processing the pressure-wave signal S5 thereby to issue an electric image signal S6 representative of the radiation image stored in the image sensor 33. The image signal S6 can be used to display the radiation image on a display such as a CRT or record the radiation image on a photosensitive material through a light-scanning recorder. Prior to such image reproduction, the image signal S6 may temporarily be recorded on an information storage medium such as a magnetic tape, a magnetic disc, or an optical disc.

After the recorded image has been converted into the electric image signal S6, the erase light source 37 is energized to cause the image sensor 33 to be exposed to the erasing light 48 from the erase light source 37 via the movable mirror 35. Any remanent radiation image which may have remained on the image sensor 33 after the pressure wave has been generated and detected can therefore be discharged from the image sensor 33, which can then be reused. A new radiation image can thereafter be recorded on the image sensor 33 and reproduced therefrom by repeating the foregoing process.

The microphone 46 positioned in the vicinity of the image sensor 33 may be replaced with a bolometer for detecting thermal energy emittted from the image sensor 33 in proportion to the pressure wave, or an electrostrictive device, or a piezoelectric device capable of electrically detecting pressure. The piezoelectric device can be composed of a piezoelectric material such as crystal, Rochelle salt, potassium tartrate (DKT), potassium primary phosphate (KDT), PZT, polyvinylidene fluoride (PVDF), or polyvinylidene cyanide copolymer [P(VDCN VAc)].

Figure 7:
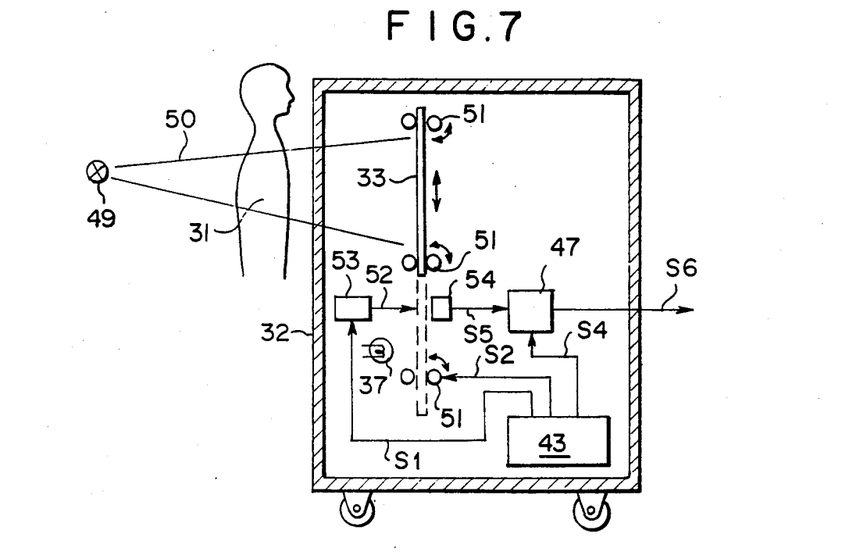
FIG. 7 is a schematic side elevational view of a camera according to another embodiment of the present invention.
Figure 8:
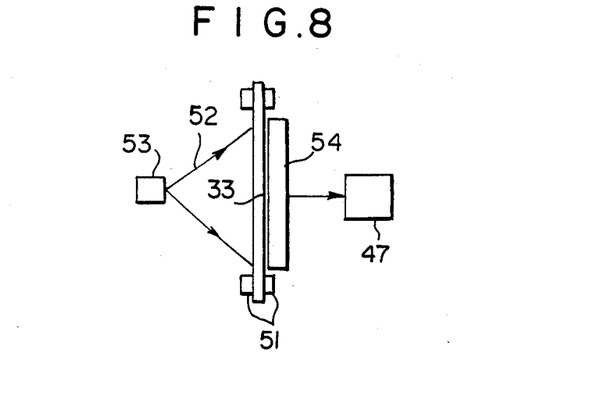
FIG. 8 is a plan view of a portion of the camera shown in FIG. 7.

FIGS. 7 and 8 illustrate an acousto-optic camera according to another embodiment of the present invention. The image sensor 33 is vertically movable by a plurality of driver rollers 51 between an upper position indicated by the solid line and a lower position indicated by the dotted line. After the radiation image of the object 31 has been recorded on the image sensor 33, the image sensor 33 is moved from the upper position downwardly to the lower position by the drive rollers 40. While the image sensor 33 is moving downwardly, a pulsed fan beam 52 is applied by a fan beam generator 53 to the image sensor 33, which then generates a pressure wave that is detected by a one-dimensional pressure-wave detector 54 comprising an array of piezoelectric devices or electrostrictive devices. The one-dimensional array detector 54 issues an electric pressure-wave signal S5 which is then processed by the signal processor 47 into an image signal S6 for reproducing the radiation image as a visible image.

Figure 9:
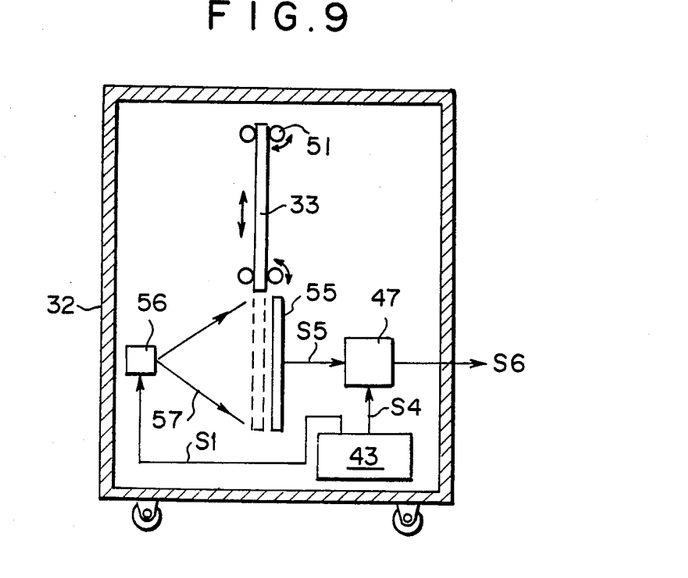
FIG. 9 is a schematic side elevational view of a camera according to still another embodiment of the present invention.

According to still another embodiment shown in FIG. 9, a two-dimensional pressure-wave detector 55 comprising a matrix of piezoelectric devices or electrostrictive devices is employed to detect the pressure wave generated by the image sensor 33. A light source 56 applies pulsed light 57 in a two-dimensional pattern to the image sensor 33. When the image sensor 33 with a recorded radiation image stored therein is moved by the drive rollers 51 from the upper solid-line position toward the lower dotted-line position, the image sensor 33 is exposed to the pulsed light from the stimulating-light source 56. After the pressure wave has been emitted from the image sensor 33 and detected by the pressure-wave detector 55, the light source 56 is energized again to apply the light to the image sensor 33 to discharge any residual radiation energy from the image sensor 33 so that the image sensor 33 can be recycled. The light source 56 thus doubles as an erase light source. Even with the matrix pressure-wave detector 55 used, the image sensor 55 may be scanned by a laser beam spot or a fan laser beam.

In the embodiments shown in FIGS. 6 through 9, the image sensor 33 is recycled by repeating the steps of recording a radiation image on the image sensor 33, reading the recorded radiation image from the image sensor 33, and erasing any residual radiation energy from the image sensor 33. However, the image sensor 33 may be replaced with a new image sensor each time a new radiation image is to be recorded, and the residual radiation energy may be erased from the image sensor 33 by a separate erase device.

Figure 10:
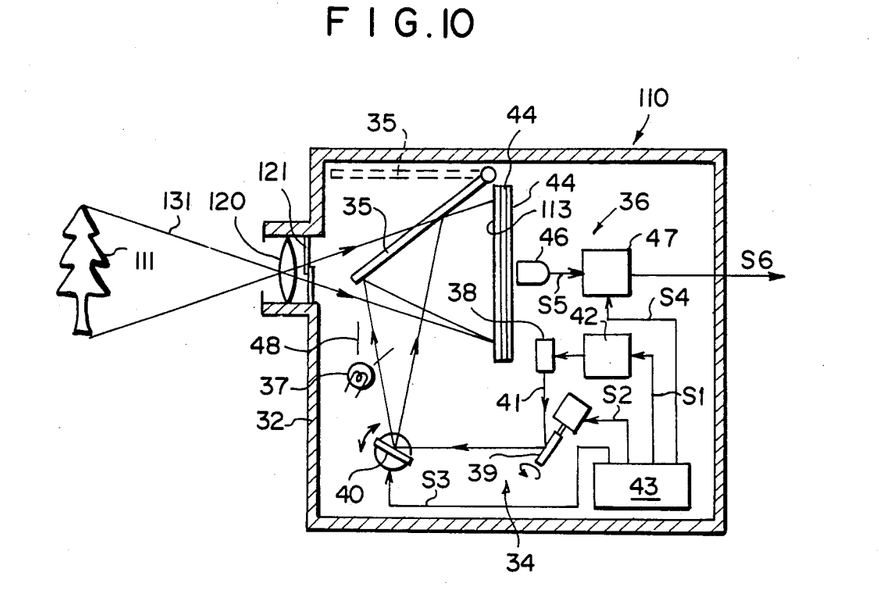
FIG. 10 is a schematic side elevational view of a camera according to a still further embodiment of the present invention.

FIG. 10 shows an acousto-optic camera according to a still further embodiment of the present invention. The acousto-optic camera, generally denoted at 110, can record an ordinary optical image. The acousto-optic camera 110 has an image sensor 113 made of photochromic glass containing silver halide for increasing the optical density upon exposure to light. The acousto-optic camera 110 also has a lens 120 and a shutter 121 which are positioned in confronting relation to the image sensor 113. When the shutter 121 is opened with the movable mirror 35 positioned as indicated by the dotted line, the image of an object 111, borne by light 131, is formed by the lens 120 on the image sensor 113. The image sensor 113 now stores the optical image of the object 113 thereon. The stored optical image can be read from the image sensor 113 by the same arrangement as that of the camera 30 shown in FIG. 6 to produce an image signal S6 representative of the recorded optical image. The image signal S6 can then be used to reproduce the image of the object 111 on a CRT or otherwise store the image on a suitable recording medium.

After the optical image has been read, the image sensor 113 is exposed to the erasing light 48 emitted from the erase light source 37 to discharge a visible-light energy from the image sensor 113 to allow the same to be recycled.

The image sensor 113 may be vertically moved between a recording position and a read-out position as shown in FIGS. 7 or 9. The photochromic glass containing silver halide, which the image sensor 113 is made of, may be formed of $SiO_2$, $Na_2O$, $Al_2O_3$, $B_2O_3$, $Li_2O$, $PbO$, $BaO$, $ZrO_2$, $Ag$, $Br$, $Cl$, $F$, and $Cu$.

Although certain preferred embodiments have been shown and described, it should be understood that many changes and modifications may be made therein without departing from the scope of the appended claims.

We claim:

1. A method of forming an acousto-optic image by using a plate-like image sensor capable of increasing its optical density upon exposure to a radiation, said method comprising the steps of:
   exposing said image sensor to a radiation bearing image information to record the image information on said image sensor;
   applying pulsed light to said image sensor to enable the same to generate a pressure wave commensurate with the recorded image information;
   detecting the pressure wave in synchronism with said pulsed light to convert said pressure wave into an electric signal; and
   reproducing an image from said electric signal.

2. A method according to claim 1, wherein said pulsed light is applied to said image sensor by scanning the image sensor with a light beam spot.

3. A method according to claim 2, wherein said pressure wave is detected by a detector capable of detecting the pressure wave produced by a portion of said image sensor which is scanned by said light beam spot.

4. A method according to claim 1, wherein said pulsed light is applied to said image sensor by scanning the image sensor with a fan beam.

5. A method according to claim 4, wherein said pressure wave is detected by a one-dimensional array detector capable of detecting the pressure wave produced by a portion of said image sensor which is scanned by said fan beam.

6. A method according to claim 1, wherein said pulsed light is applied to said image sensor over its entire surface.

7. A method according to claim 6, wherein said pressure wave is detected by a two-dimensional matrix detector capable of detecting the pressure wave produced by the entire surface of said image sensor which is exposed to said pulsed light.

8. A method according to claim 1, wherein said pressure wave is detected by a microphone.

9. A method according to claim 1, wherein said pressure wave is detected by a bolometer.

10. A method according to claim 1, wherein said pressure wave is detected by a piezoelectric device.

11. A method according to claim 1, wherein said pressure wave is detected by an electrostrictive device.

12. A method according to claim 1, wherein said image sensor comprises a stimulable phosphor sheet.

13. A method according to claim 1, wherein said image sensor comprises a sheet made of a photochromic material.

14. A method according to claim 13, wherein said photochromic material is photochromic glass.

15. A device for forming an acousto-optic image, comprising:
   a plate-like image sensor capable of increasing its optical density upon exposure to a radiation;
   first exposure means for exposing said image sensor to a radiation bearing image information to record the image information on said image sensor;
   second exposure means for applying pulsed light to said image sensor to enable the same to generate a pressure wave commensurate with the recorded image information;
   detecting means for detecting the pressure wave in synchronism with said pulsed light to convert said pressure wave into an electric signal; and
   image reproducing means for reproducing an image from said electric signal.

16. A device according to claim 15, wherein said detecting means comprises a microphone.

17. A device according to claim 15, wherein said detecting means comprises a bolometer.

18. A device according to claim 15, wherein said detecting means comprises a piezoelectric device.

19. A device according to claim 15, wherein said detecting means comprises an electrostrictive device.

20. A device according to claim 15, wherein said image sensor comprises a stimulable phosphor sheet.

21. A device according to claim 15, wherein said image sensor comprises a sheet made of a photochromic material.

22. A device according to claim 21, wherein said photochromic material is photochromic glass.

23. An acousto-optic camera comprising:
a light-shielding housing for accommodating a plate-like image sensor capable of increasing its optical density upon exposure to a radiation, said light-shielding housing having means for exposing said image sensor to a radiation bearing image information to record the image information on said image sensor;
exposing means in said light-shielding housing for applying pulsed light to said image sensor to enable the same to generate a pressure wave commensurate with the recorded image information; and
detecting means in said light-shielding housing for detecting the pressure wave in synchronism with said pulsed light to convert said pressure wave into an electric signal.

24. An acousto-optic camera according to claim 23, wherein said detecting means comprises a microphone.

25. An acousto-optic camera according to claim 23, wherein said detecting means comprises a bolometer.

26. An acousto-optic camera according to claim 23, wherein said detecting means comprises a piezoelectric device.

27. An acousto-optic camera according to claim 23, wherein said detecting means comprises an electrostrictive device.

28. An acousto-optic camera according to claim 23, wherein said image sensor comprises a stimulable phosphor sheet.

29. An acousto-optic camera according to claim 23, wherein said image sensor comprises a sheet made of a photochromic material.

30. An acousto-optic camera according to claim 23, wherein said photochromic material is photochromic glass.

31. An acousto-optic camera according to claim 23, including erasing means in said light-shielding housing for applying erasing light to said image sensor to erase a residual radiation energy from the image sensor after the pressure wave generated therefrom has been detected by said detecting means.

32. An acousto-optic camera according to claim 23, including switching means in said light-shielding housing for selectively exposing said image sensor to said radiation and said pulsed stimulating light.

33. An acousto-optic camera according to claim 32, wherein switching means comprises a movable mirror angularly movable between a first position in which said image sensor can be exposed directly to said radiation and a second position in which said image sensor can be exposed to said pulsed light as reflected by said movable mirror.

34. An acousto-optic camera according to claim 32, wherein switching means comprises a plurality of rollers for moving said image sensor between a first position in which said image sensor can be exposed directly to said radiation and a second position in which said image sensor can be exposed to said pulsed light.

35. An acousto-optic camera according to claim 33, wherein said exposing means comprises a light source for generating a pulsed fan beam to be applied to said image sensor.

36. An acousto-optic camera according to claim 33, wherein said exposing means comprises a light source for generating pulsed stimulating light in a two-dimensional pattern to be applied to said image sensor over its entire surface.

37. An acousto-optic camera according to claim 23, wherein said radiation is a nonvisible radiation.

38. An acousto-optic camera according to claim 23, wherein said radiation is visible light.

* * * * *